United States Patent
Zhu et al.

(10) Patent No.: US 9,517,435 B2
(45) Date of Patent: Dec. 13, 2016

(54) FORMALDEHYDE ABSORBENT AND METHOD FOR USING THE SAME

(71) Applicant: NINGBO YUCHEN ENVIROCLEAN TECH CO., LTD, Ningbo (CN)

(72) Inventors: Zuolin Zhu, Ningbo (CN); JiaBao Zhao, Ningbo (CN); Meng Sun, Ningbo (CN); Zhenji Zhu, Ningbo (CN); Kangfu Gu, Ningbo (CN); Shanqing Sun, Ningbo (CN); Tongxing Xie, Ningbo (CN); Wenhai Wang, Ningbo (CN)

(73) Assignee: NINGBO YUCHEN ENVIROCLEAN TECH CO., LTD., Ningbo (CN)

( * ) Notice: Subject to any disclaimer, the term of this patent is extended or adjusted under 35 U.S.C. 154(b) by 315 days.

(21) Appl. No.: 14/119,754

(22) PCT Filed: Sep. 29, 2013

(86) PCT No.: PCT/CN2013/084570
§ 371 (c)(1),
(2) Date: Nov. 22, 2013

(87) PCT Pub. No.: WO2015/042902
PCT Pub. Date: Apr. 2, 2015

(65) Prior Publication Data
US 2015/0086458 A1    Mar. 26, 2015

(30) Foreign Application Priority Data

Sep. 24, 2013    (CN) .......................... 2013 1 0438200

(51) Int. Cl.
*B01D 53/02* (2006.01)
*B01D 53/72* (2006.01)
(Continued)

(52) U.S. Cl.
CPC .............. *B01D 53/72* (2013.01); *B01D 53/02* (2013.01); *B01D 53/78* (2013.01); *B01D 53/82* (2013.01);
(Continued)

(58) Field of Classification Search
CPC ............ B01D 2251/70; B01D 2251/80; B01D 2252/20494; B01D 2253/20; B01D 2257/708; B01D 2257/93; B01D 2258/06; B01D 2259/4508; B01D 53/02; B01D 53/1487; B01D 53/1493; B01D 53/72; B01D 53/78; B01D 53/82
See application file for complete search history.

(56) References Cited

U.S. PATENT DOCUMENTS 5,231,063 A     7/1993  Fukumoto et al.
5,698,108 A *  12/1997  Okun ...................... C02F 1/56
                                                         210/702
(Continued)

FOREIGN PATENT DOCUMENTS

CN        101138671       3/2002
CN        101007203       8/2007
(Continued)

OTHER PUBLICATIONS

Indoor Air Quality Control Techniques, by Jeffrey M. Lemn, 1987, William Andrew Press, pp. 183-184.
(Continued)

*Primary Examiner* — Christopher P Jones
(74) *Attorney, Agent, or Firm* — Hamre, Schumann, Mueller, Larson, P.C.

(57) ABSTRACT

The present invention discloses a formaldehyde absorbent and a method for using the same, the chemical composition of the formaldehyde absorbent by weight percentage is, amino acid: 0.1-99.9%; DNA and RNA base 99.9-0.1%. The
(Continued)

method comprises the following steps: a. dissolving the formaldehyde absorbent in solvent to form a solution or dissolving the formaldehyde absorbent in solvent and mixing the same onto a solid carrier; b. placing the solution or solid carrier in indoor space that contains formaldehyde; and c. contacting and reacting the formaldehyde-containing air with the solution or the solid carrier and then absorbing the same. The present invention not only achieves not only excellent performance in absorbing hazard gases in the air, but also features low-cost, and further causes no secondary pollution, which therefore creates great social and economical significance in improving quality of human life, safeguarding human health, and protecting environment.

14 Claims, 2 Drawing Sheets

(51) Int. Cl.
  B01D 53/78 (2006.01)
  B01D 53/82 (2006.01)
(52) U.S. Cl.
  CPC ....... *B01D 2251/70* (2013.01); *B01D 2251/80* (2013.01); *B01D 2252/20494* (2013.01); *B01D 2253/20* (2013.01); *B01D 2257/708* (2013.01); *B01D 2257/93* (2013.01); *B01D 2258/06* (2013.01); *B01D 2259/4508* (2013.01)

(56) References Cited

U.S. PATENT DOCUMENTS

| | | | |
|---|---|---|---|
| 2008/0286472 | A1* | 11/2008 | Tutin ............... A62D 3/33 427/350 |
| 2009/0258042 | A1* | 10/2009 | Anastasiou ........... A61K 8/11 424/401 |

FOREIGN PATENT DOCUMENTS

| | | |
|---|---|---|
| CN | 101648109 | 2/2010 |
| CN | 103120892 | 5/2013 |
| JP | H02115020 | 4/1990 |
| JP | 2011-110079 | 6/2011 |

OTHER PUBLICATIONS

Indoor Air Quality Control Techniques, by Jeffrey M. Lemn, 1987, William Andrew Press, pp. 200-201.

* cited by examiner

FORMALDEHYDE ABSORBENT AND METHOD FOR USING THE SAME

FIELD OF THE INVENTION

The present invention relates to a formaldehyde absorbent and a method for using the same, and particularly relates to an absorbent that is able to absorb formaldehyde in the air actively, high efficiently and completely.

BACKGROUND OF THE INVENTION

Most people spend most time of life indoors. Therefore, quality of the indoor air plays a very important role in people's life. With the continuously increase of population, the deteriorative shortage of natural resources, and the worsening environmental pollution, the concentration of volatile organic compounds (VOCs) in the air which is one of the main causes to formation of PM2.5 particles that affect the air quality and human health increases significantly. The volatile organic compounds in the air include formaldehyde, acetaldehyde, various ketones, aromatic hydrocarbon, and the like. In these volatile organic compounds, formaldehyde is the most common one, and comes from synthetic fibers such as artificial carpet and artificial cloth), resin such as adhesive for furniture), paint (used for wall decoration and furniture paint), microorganism degradation (indoor space is particularly suitable for microorganisms' growth and reproduction because of the suitable humidity and rich nutrition), meat, fruit and vegetables, and various wood.

Irritation caused by formaldehyde may lead to acute lesion of headache, nausea, asthma and skin rash, and formaldehyde is the organic matter that most easily changes protein and the genetic material such as DNA and RNA, leads to tumor and cancer, and causes great harm to the human body. Removing the formaldehyde indoor (including in the car) and reducing the formaldehyde to a safety concentration range are very important for protecting the human life and the genetic substances.

The concentration of formaldehyde indoor that is acceptable by the World Health Organization (WHO) is 0.08 ppm, and formaldehyde concentration in most Chinese indoor space is much higher than this value. The concentration of formaldehyde in new furniture and decoration housing even reaches hundreds of ppm and goes beyond the standard by tens of thousands of times, which becomes the main cause to the increase of incidence of tumor and cancer in China in recent years.

In order to eliminate the hazards caused by the formaldehyde, one way readily occurred to people is to avoid the substances which product formaldehyde. Urea-formaldehyde resin polymer (UF) is considered a major villain. However, the Canadian research shows that the concentration of formaldehyde is the same in a room where the UF is used and as in a room where the UF material is not used (Ref. Indoor Air Quality Control Techniques, by Jeffrey M. Lemn, in 1987, William Andrew Press). Subsequently, the ban on use of this substance was canceled one year later (in 1983). Afterwards, the materials containing formaldehyde were in use all the time for the low cost and high performance (very high performance cost ratio) thereof. Therefore, people have attempted a variety of coating technologies, and these technologies have not been widely used due to high cost and poor effect. Some other methods for actively removing formaldehyde, including dehumidification, air washing, ammonia fumigation, and the like, have not been promoted due to poor effect, large energy consumption, or secondary pollution. For example, the ammonia water elution may directly cause injury to human body and damages to furniture and housing).

Therefore, there are two main research directions at present, adsorption, and oxidation.

The absorbent materials include activated carbon, carbon fiber, activated aluminum oxide, treated calcium carbonate, sepiolite, ceramic materials, wool, lignin, mesoporous silica materials, and the like. Meanwhile, the adsorption materials have been modified using a variety of chemicals to further strengthen the formaldehyde adsorption capability, for example, immersion in urea or ammonia sulfate, atmospheric oxidation, carry onto zinc chloride, treatment with hydrochloric acid and ferrous powder after treatment with nitric acid, modification by amino silane or nanometer silver powder, phosphoric acid activation, treatment with potassium hydrogen phosphate, and the like.

All of these methods have failed to be widely employed because adsorption effects of formaldehyde are poor, or the raw materials are toxic to the environment and human, or the cost is too high, except that the active carbon is accepted as a type of formaldehyde adsorption product by most people. According to the research of the United States in 1983 (Ref. Indoor Air Quality Control Techniques, by Jeffrey M. Lemn, in 1987, William Andrew Press), each family needs to remove hundreds of grams of formaldehyde a year. The adsorption capability of the activated carbon is limited due to the absorption using the activated carbon is reversible and is subject to impacts from the ambient temperature, humidity, and other molecules. An annual cost of each family reaches $600 according to the price of activated carbon at that time. In consideration of factors such as inflation, the annual cost of using active carbon amounts up to $2,000.

Because formaldehyde can be oxidized to formic acid, the oxidation method is an important way to remove formaldehyde. The method includes using oxidant directly, producing ozone or free radical by using a high voltage electric field, and the chemical catalytic oxidation method invented by the inventor of the present invention. With respect to the oxidation method, since the ionization potential of formaldehyde is up to 10.88 eV which is very close to that of the oxygen (12.07 eV), strong oxidants need to be used to oxidize formaldehyde. These oxidants include potassium permanganate, peroxy-acid, peroxy-alcohol, hydrogen peroxide, dichromate, copper peroxide, chromium oxide, and the like. However, these oxidants have significant drawbacks. In one aspect, these oxidants have such strong oxidation capabilities that other components in the air may be oxidized during oxidation of formaldehyde, causing quick deactivation of the oxidants, and therefore the cost is very high (there is application of carrying the oxidants to the solid carrier. In another aspect, all of the oxidants may cause secondary pollution, and the metal oxidants may cause heavy metal pollution to the environment. Furthermore, the peroxy-acid and peroxy-alcohol are volatile and the volatile substance may corrode the other articles and cause damages the human body. In still another aspect, the by-products of formaldehyde oxidization are more volatile, and thus more harmful to environment and human body. Meanwhile, the strong oxidants tend to explode. In view of the above, the oxidation method can not be promoted. The bi-enzymatic method belongs to the oxidation methods, but the cost is too high for household use. The high voltage electric field method includes negative ion, photo-catalytic, ozone, and the like. These methods all have drawbacks. The formaldehyde removal effect of the negative ion method is only 18-30% due to a weak oxidization capability thereof, and thus the negative ion method needs to be run for a very long time at a low indoor temperature (The process of negative on generating produces heat, leading to a high overall energy consumption). Like the bi-enzymatic method, the cost of using photo-catalytic is the highest because the carrier is nanotitania.

In addition, the hydroxyl free radical that produced in the photo-catalytic method is harmful to human body and environment. Although the cost of ozone method is relatively low, ozone will cause damages the human health and pollute the environment. The capability of removing formaldehyde in the chemical catalytic oxidation method is several to ten times higher than that of the activated carbon.

Therefore, to invent a method of removing formaldehyde which is cost-efficiency, causes no secondary pollution, and achieves a superior effect over the activated carbon is social and economically and socially significant in improving quality of human life, safeguarding human health, and protecting environment.

SUMMARY OF THE INVENTION

The present invention provides a formaldehyde absorbent and a method for using the same, which overcome the drawbacks of the prior art, such as high cost, non-ideal removal effect and secondary pollution.

In order to achieve the objective, the present invention provides a formaldehyde absorbent, and the chemical composition of the formaldehyde, absorbent by weight percentage is 0.1-99.9% amino acid, 99.9-0.1% DNA and RNA base.

Preferably, the amino acid is selected from the group consisting of alanine, valine, leucine, isoleucine, proline, phenylalanine, tryptophan, methionine, glycine, serine, threonine, tyrosine, cysteine, asparagine, glutamine, arginine, histidine, aspartic acid, glutamic acid, or any combination thereof.

Preferably, the DNA and RNA base is selected from the group consisting of adenine, guanine, cytosine, thymine, uracil, or any combination thereof.

Preferably, aid amino acid is an amino acid metal salt, wherein the amino acid metal salts comprise alkali metal salts, alkaline earth metal salts, and transition metal salts.

Preferably, the alkali metal salts comprise lithium salt, sodium salt, potassium salt, rubidium salt or cesium salt; the alkaline earth metal salts comprise beryllium salt, magnesium salt, calcium salt, strontium or barium salt; and the transition metal salts comprise ferric salt and zinc salt.

Preferably, the formaldehyde absorbent also comprises 0.1-10% water-soluble inorganic salt.

Preferably, the water-soluble inorganic salt is a silicon, oxygen and aluminum compound, or a silicon, oxygen and sodium compound, or a silicon, oxygen and potassium compound, or a silicon, oxygen, aluminum and sodium compound, or a silicon, oxygen, aluminum, and potassium compound, or an oxygen, silicon, potassium and sodium compound.

Preferably, a pH value of the formaldehyde absorbent is from 7.5 to 12.5.

Preferably, a pH value of the formaldehyde absorbent is from 9 to 11.

Preferably, the formaldehyde absorbent further comprises an additive, wherein the additive comprises essence, pigment and antiseptic.

In order to achieve the above objective, the present invention provides a method for using formaldehyde absorbent, wherein the method comprises the following steps:

a. dissolving the formaldehyde absorbent in solvent to form a solution or dissolving the formaldehyde absorbent in solvent and mixing the same onto a solid carrier;

b. placing the solution or solid carrier in indoor space that contains formaldehyde;

c. contacting and reacting the formaldehyde-containing air with the solution or the solid carrier and then absorbing the same.

Preferably, the solvent comprises water and protic solvent.

Preferably, the protic solvent comprises glycerol, glycerol derivative and ionic liquid.

Preferably, the solid carrier is cloth or cotton paper.

Preferably, the solution in step b is arranged in a container, and stirred constantly when the solution is placed in indoor space that contains formaldehyde.

Compared with the prior art, the products of the present invention are strong formaldehyde absorbents but not passive formaldehyde adsorbent. The method of removing formaldehyde which is cost-efficiency, causes no secondary pollution, and achieves a superior effect over the activated carbon is social and economically and socially significant in improving quality of human life, safeguarding human health, and protecting environment.

DETAILED DESCRIPTION OF THE INVENTION

Figure 1:
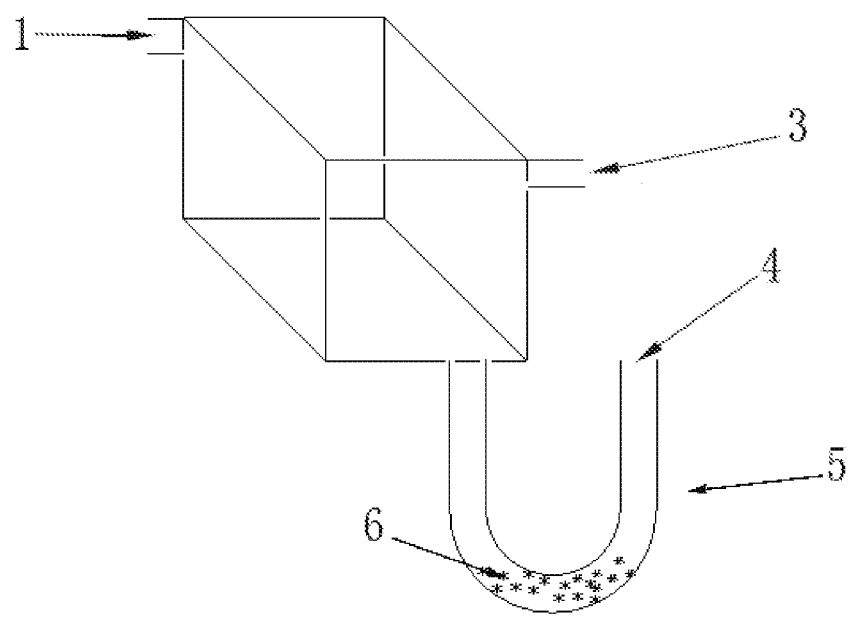
FIG. 1 is the structure of the formaldehyde absorption capability measurement device of the present invention.

Embodiments of the present invention are further described with reference to the attached drawings and examples. The following examples are used to illustrate the present invention, but are not intended to limit the scope of the present invention.

After small molecule aromatic products are extracted by using aromatic alcohol at a pH of 4, and small molecule organic acid products are extracted by using fatty alcohol at a pH of 2 from the hydrolysis products of sawdust and other plants, the organic substances are found in an aqueous solution. The solution is evaporated in a low temperature and negative pressure environment to obtain a viscous semi-solid product. The excellent performance of absorbing formaldehyde in the air is found by chance, and the lowest absorption capability is one hundred times that of the activated carbon. The absorbent has never been disclosed in any literature or been conferred.

Through extensive and deep research, and comparison with known compounds, such as element analysis, H-NMR, C-NMR, and liquid chromatography, the separated organic matter is a mixture, whose components are amino acids, DNA and RNA bases, and water-soluble inorganic salts that contain silicon, oxygen and/or aluminum, sodium, and/or potassium. The content of water-soluble inorganic salt is generally from 0.1 to 10%, which depends on the different plants. Correspondingly, the total content of water-soluble inorganic salts, amino acids, DNA and RNA bases together is 100%.

After analyzing and confirming these organic compounds, a mixture thereof is prepared by using pure amino acids and DNA/RNA bases, and it has been found that the mixture has excellent performance of absorbing formaldehyde in the air as the product that has been separated. The formaldehyde absorption capability is closely related to the pH value of the mixture, and is also related to components thereof. If the mixture is formed of pure amino acid, or pure base, or the mixture contains no water-soluble inorganic salt, the performance of absorbing formaldehyde is poorer than the mixture.

A formaldehyde absorbent according to the present invention is brand-new, natural and high performance cost ratio. The chemical composition of the formaldehyde absorbent by weight percentage is 0.1-99.9% amino acid; and 99.9-0.1% DNA and RNA base. The amino acid is selected from the group consisting of alanine, valine, leucine, isoleucine, proline, phenylalanine, tryptophan, methionine, glycine, serine, threonine, tyrosine, cysteine, asparagine, glutamine, arginine, histidine, aspartic acid, and glutamic acid, or any combination thereof. The DNA and RNA base is selected from the group consisting of adenine, guanine, cytosine, thymine, and uracil, or any combination thereof.

The amino acid is a kind of amino acid metal salts, and the amino acid metal salts include alkali metal salts, alkaline earth metal salts and transition metal salts, except heavy metallic salt. Alkali metal salts are lithium salt, sodium salt, potassium salt, rubidium salt or cesium salt, and alkaline earth metal salts are beryllium salt, magnesium salt, calcium salt, strontium or barium salt, and transition metal salts are ferric salt or zinc salt.

The formaldehyde absorbent also comprises 0.1-10% water-soluble inorganic salt. The water-soluble inorganic salt is a silicon, oxygen and aluminum compound, or a silicon, oxygen and sodium compound, or a silicon, oxygen and potassium compound, or a silicon, oxygen, aluminum and sodium compound, or a silicon, oxygen, aluminum, silicon and potassium compound, or a oxygen, potassium and sodium compound.

The pH value of the formaldehyde absorbent is from 7.5 to 12.5. Preferably, the pH value of the formaldehyde absorbent is from 9 to 11. If the pH value is below a value within this range, it is not preferable because the absorption capability is poorer even if the formaldehyde absorbent according to the present invention achieves a much better effect than that activated carbon. If the pH value is above a value within this range, it is also not preferable because the solution is corrosive even if a sound absorption effect can be achieved.

The formaldehyde absorbent further comprises an additive, wherein the additive comprises essence, pigment and antiseptic.

The present invention provides a method for using formaldehyde absorbent, and the method comprises the following steps:

a. dissolving the formaldehyde absorbent in solvent to form a solution or dissolving the formaldehyde absorbent in solvent and mixing the same onto a solid carrier;

b. placing the solution or solid carrier in indoor space that contains formaldehyde;

c. contacting and reacting the formaldehyde-containing air with the solution or the solid carrier and absorbing the same.

The solvent comprises water and protic solvent. The protic solvent comprises glycerol, glycerol derivative and ionic liquid.

The solid carrier is cloth or cotton paper, and it is placed or hung in the room where formaldehyde needs to be adsorbed. Then formaldehyde reacts with the solid carrier and is absorbed from the air.

The solution of step b is contained in a container having a larger surface area, and needs to be constantly stirred when being placed in indoor space that contains formaldehyde. In such a case, the formaldehyde reacts with the solution and is absorbed from the air.

High Performance Liquid Chromatography (HPLC) is used to detect the amino acids and DNA/RNA bases. All the samples of amino acids and bases are prepared to be 1.0 µg/mL, and an evaporative light scattering detector (ELSD) is used for the detection. A mobile phase A is 0.1% trifluoroacetic acid, and a mobile phase B is acetonitrile, and the phase gradient is (controlled by using the mobile phase B): B % is 2% within 0-10 minutes, B % amounts from 2% to 30% within 10-25 minutes, B % amounts from 30% to 100% within 25-26 minutes, B % maintains at 100% within 26-26.5 minutes, B % decreases 100% to 2% within 26.5-27 minutes, and B % maintains at 2% within 27-30 minutes. The column is Premier AQ, 5 µm, 150×4.6 mm, and the injection volume is 10 µL, the flow rate is 1 ml/min, the column temperature is 30'C, and the detector is set to Gain=5, temperature=35° C., pressure=250 kPa.

Unless otherwise specified, various raw materials according to the present invention may be commercially obtained or be prepared according to the conventional method in the art. Unless otherwise defined, all professional and scientific terms or expressions herein have the same meanings as what are readily occurred to persons of ordinary skilled in the art. Additionally, any method and material similar or equivalent to the disclosure of the present invention may be applied for the present invention.

The present invention is further illustrated with reference to specific embodiments. In the following examples, with respect to experimental methods with no specific conditions, national standards of measurement apply. If no corresponding national standards are given, universal international standards, universal conditions, or manufacturer's conditions apply. Unless otherwise specified, all the components are measured by weight, and all the percentages are weight percentages, the molecular weight numbers of the polymer are average molecular weights.

Example 1

The product according to the present invention has powerful capability in absorbing formaldehyde. The mixture of amino acids and bases separated from the full hydrolyses of pine sawdust comprises alanine (Ala), valine (Val), leucine (Leu), isoleucine (Ile), proline (Pro), phenylalanine (Phe), tryptophan (Trp), methionine (Met), glycine (Gly), serine (Ser), threonine (Thr), cysteine (Cys), tyrosine (Tyr), asparagine (Asn), glutamine (Gin), arginine (Arg), histidine (His), aspartic acid (Asp), glutamic acid (Glu) and adenine (A), guanine (G), cytosine (C), thymine(T), uracil (U) and water-soluble inorganic salts (the element is a silicon, oxygen and aluminum compound, or a silicon, oxygen and sodium compound, or a silicon, oxygen and potassium compound, or a silicon, aluminum, oxygen and sodium compound, or a silicon, oxygen, aluminize n, silicon and potassium compound, or an oxygen, potassium and sodium compound. The remaining ash in the organic matter is removed by calcinations, and the content is 7.3%).

An aqueous solution of 10% was prepared by taking 50 g the mixture, and the pH of the solution was adjusted by using sodium hydroxide. As shown in FIG. 1, the formaldehyde absorption capability was absolute absorption, and the sealed stainless steel box (0.7 m×0.7 m×0.7 m) was used as the spatial determination of formaldehyde for test. An outlet 4 of a stainless steel box 5 was a U-shape tube, and the bottom of the tube was filled with an activated carbon or a liquid material 6. The activated carbon served as a reference to measure the capability in absorbing formaldehyde. The two tests were simultaneous performed for case of comparison. The bottom of one U-shape tube was filled with the prepared solution (pH=1.5), while the bottom of another was filled with 500 g food grade activated carbon for formaldehyde adsorption, and then a formaldehydemeter (PPM Formaldehydemeter 400, with a resolution of 0.01 ppm) was connected to a detector interface 3 to detect the changes of formaldehyde concentration in the boxes.

The test boxes were sealed, and the air which contains 1.0 ppm of formaldehyde was supplied to the boxes continuously to fill the boxes with the air containing formaldehyde until the concentration of formaldehyde, in the boxes no longer reduces. Finally, the total volume of the air was recorded to calculate the amount of formaldehyde absorbed, and by dividing the amount of formaldehyde by the total amount of absorbent (activated carbon=500 g, the absorbent=50 g), the absorption capabilities of activated carbon and formaldehyde absorbent were respectively calculated as listed Table 1.

TABLE 1

Data comparison of absorption capability formaldehyde in the air

| Test No. | Activated Carbon (mg/g) | Absorbent (mg/g) |
| --- | --- | --- |
| 1 | 0.5 | 218 |
| 2 | 1.1 | 276 |
| 3 | 0.7 | 193 |

According to the results, the absorption capability of the absorbent was 200 times greater than that of the activated carbon.

Example 2

The product according to the present invention was formaldehyde absorbent. 100 ml of the 10% solution (contains 10 g formaldehyde absorbent) prepared in EXAMPLE 1 was used and the pH of the solution was adjusted to 10.5 with sodium hydroxide. According to the calculation that the absorption capability of the absorbent was 200 times greater than that of activated carbon. 2 kg of activated carbon was used.

The absorption capability changed with the concentration of formaldehyde, and the space to the test was some sealing boxes (1.0 m×1.0 m×1.0 m). Aqueous solution of the present invention was placed in a box with stirring by magnetic spin, and activated carbon was placed in another box. Both of the initial formaldehyde concentrations were 2 ppm, and the temperature in the room was maintained at 25° C. Then the concentrations in the two boxes are monitored by taking sample. The values of concentrations are the average of three experimental ones, as listed in Table 2.

TABLE 2

| | Concentrations | |
| --- | --- | --- |
| Time (hours) | Activated Carbon | Absorbent |
| 0 | 2.0 | 2.0 |
| 1 | 1.12 | 0.33 |
| 2 | 1.03 | 0.15 |
| 3 | 0.59 | 0.08 |
| 4 | 0.43 | 0.05 |
| 5 | 0.36 | 0.02 |
| 6 | 0.19 | 0.01 |
| 7 | 0.18 | Below detection limit |
| 8 | 0.18 | Below detection limit |
| 9 | 0.17 | Below detection limit |
| 10 | 0.12 | Below detection limit |
| 24 | 0.08 | Below detection limit |
| 48 | 0.08 | Below detection limit |
| 72 | 0.08 | Below detection limit |
| Heat the air in boxes to 50° C. | 0.39 | Below detection limit |

The results show that the mechanism of the product according to the present invention lies in absorption, which is capable of removing formaldehyde completely. Once being absorbed, the formaldehyde cannot be released even by heating. Nevertheless, the activated carbon cannot remove formaldehyde completely because the mechanism thereof is just an adsorption and a balance, and the formaldehyde may release again once being heated.

Example 3

The absorption capability of the absorbent changes with pH.

Figure 2:
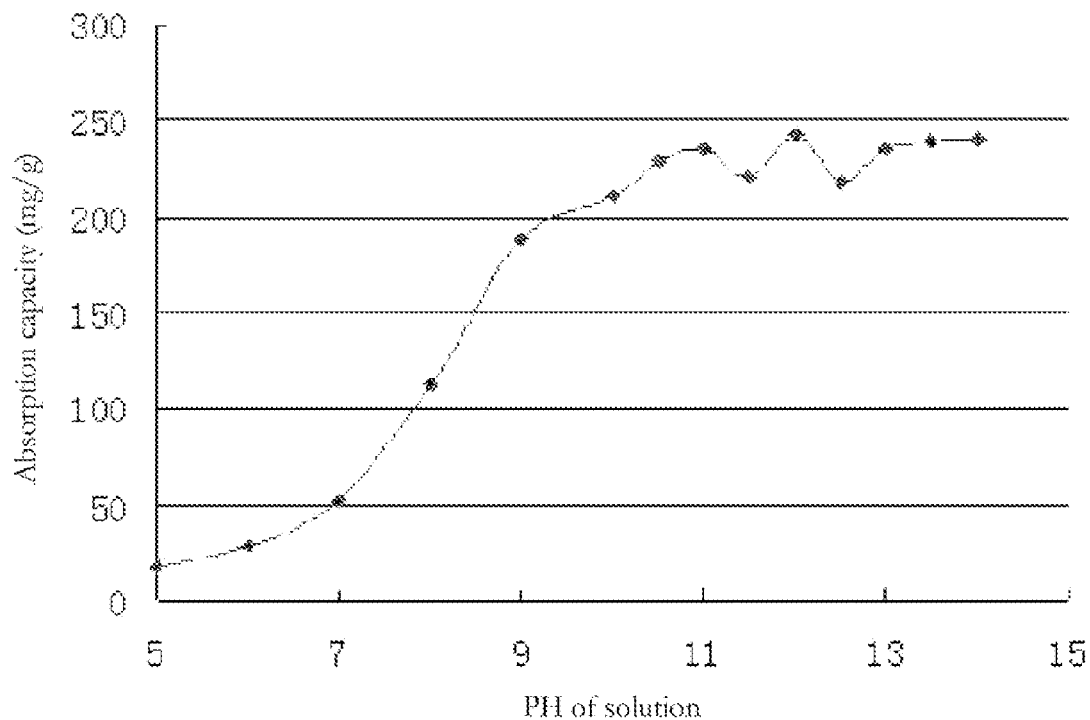
FIG. 2 is the relationship between the absorption capability of the aqueous absorbent solution and pH.

50 g of the mixture was used, and pH of solution was adjusted with sodium hydroxide, then the solutions which content is 10% and pH=5, 6, 7, 8, 9, 10, 10.5, 11, 11.5, 12, 12.5, 13, 13.5, 14 were prepared respectively The measurement method was the same as that in EXAMPLE 1, The experimental value of each pH was measured three times and the average of the three values was recorded in Table 3 below as the absorption capability. FIG. 2 shows the change of absorption capability.

TABLE 3

Data of absorption capability

| pH | Absorption Capability (mg/g) |
| --- | --- |
| 5 | 17 |
| 6 | 28 |
| 7 | 52 |
| 8 | 113 |
| 9 | 189 |
| 10 | 211 |
| 10.5 | 229 |
| 11 | 236 |
| 11.5 | 221 |
| 12 | 243 |
| 12.5 | 218 |
| 13 | 235 |
| 13.5 | 239 |
| 14 | 241 |

The results showed that the absorption capability of the absorbent was good when the pH is 9 or above.

Example 4

This example was basically the same as the second one, and the only difference was that the pH of the solution was adjusted with potassium hydroxide but not sodium hydroxide. The results showed that the absorption capability was the same as that of sodium hydroxide Example 5

The absorption capability of the absorbent changes with pH in glycerin solvent.

Figure 3:
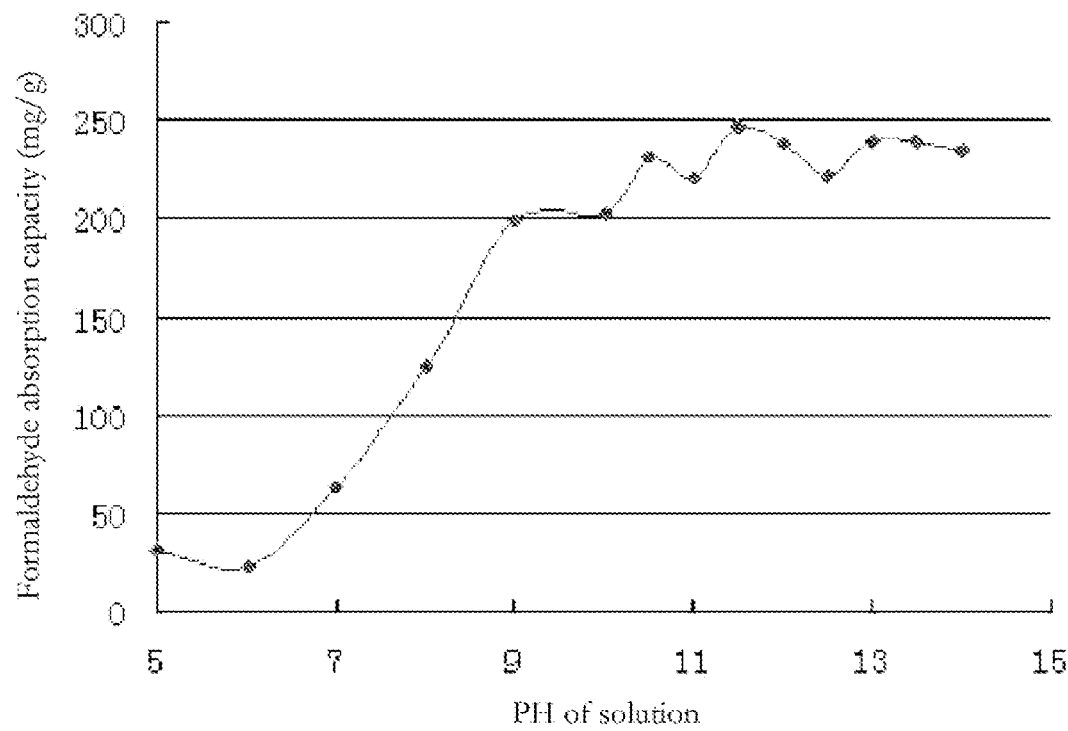
FIG. 3 is the relationship between the absorption capability of the glycerol absorbent solution and pH.

This example was substantially the same as EXAMPLE 3, and the only difference was using glycerin instead of the water solvent. 50 g of the mixture was used, and pH of solution was adjusted with sodium hydroxide, then 5% aqueous solutions where pH=5, 6, 7, 8, 9, 10, 10.5, 11, 11.5, 12, 12.5, 13, 13.5, 14 were prepared respectively. The measurement method was the same as EXAMPLE 1. The experimental value of each pH was measured three times and the average of the three values was recorded in Table 4 below as the absorption capability. FIG. 3 shows the change of absorption capability.

TABLE 4

Data of absorption capability in glycerin solvent

| pH | Absorption Capability (mg/g) |
|---|---|
| 5 | 31 |
| 6 | 22 |
| 7 | 63 |
| 8 | 125 |
| 9 | 199 |
| 10 | 203 |
| 10.5 | 231 |
| 11 | 220 |
| 11.5 | 247 |
| 12 | 238 |
| 12.5 | 222 |
| 13 | 239 |
| 13.5 | 240 |
| 14 | 235 |

The results showed that the absorption capability in non-aqueous such us glycerin was similar to that in water.

Example 6

The absorbent solution with different contents (weight ratio) of amino acids and bases respectively was prepared by using the amino acids and bases that were brought back. The representative amino acid was alanine, and the representative base was guanine. The pH value of the 10% aqueous solution was maintained at 10.5. The measurement method was the same as EXAMPLE L Each test was carried out three times and the average of the three values was recorded in Table 5 as the absorption capability.

TABLE 5

Absorption capability of prepared absorbent

| Composition (amino acid:base) | Absorption capability (mg/g) |
|---|---|
| 100:0 | 176 |
| 99.5:0.5 | 203 |
| 99:1 | 199 |
| 95:5 | 200 |
| 90:10 | 205 |
| 85:15 | 209 |
| 80:20 | 193 |
| 75:25 | 201 |
| 70:30 | 200 |
| 65:35 | 207 |

TABLE 5-continued

Absorption capability of prepared absorbent

| Composition (amino acid:base) | Absorption capability (mg/g) |
|---|---|
| 60:40 | 208 |
| 50:50 | 202 |
| 40:60 | 209 |
| 35:65 | 199 |
| 30:70 | 205 |
| 25:75 | 201 |
| 20:80 | 203 |
| 15:85 | 195 |
| 10:90 | 201 |
| 5:95 | 206 |
| 1:99 | 198 |
| 0.5:99.5 | 204 |
| 0:100 | 166 |

The results showed that the absorption capability of these compounds had no relation to the relative amount of amino acids and bases. The absorption capability of these compounds was much better than that of pure amino acid and pure base, and poorer than the product separated from plant hydrolysis. It is illustrated that the water soluble inorganic salts had strong absorption capability. Such inorganic salt was not disclosed in the literature.

Example 7

The absorbent solution with different contents (weight ratio) of amino acids and bases respectively was prepared by using the amino acids and bases that were brought back. The representative amino acid was alanine, and the representative base was guanine. The pH value of the solution with content of 10% was maintained at 10.5. Then the solution was sprayed onto Xuan papers, and the Xuan papers were placed into the U-shape tube of absorptive capacity detector as shown in FIG. 1. The measurement method was the same as EXAMPLE 1. Each test was carried out three times and the average of the three values was recorded for comparing.

The results showed that the absorption capability of the absorbent sprayed onto carrier (Xuan paper) was the same as that in water solution, and the value was 209 mg/g.

The present invention features advantages of strong capability in absorbing such hazard gases as formaldehyde in the air and cost-efficiency, and no secondary pollution. Therefore, the present invention creates great social and economic significance in improving quality of human life, safeguarding human health, and protecting environment.

All above are only preferred embodiments of the present invention. It should be noted that persons of ordinary skill in the art may make some improvements and modifications. Such improvements and modifications shall be considered as falling within the scope of the present invention.

What is claimed is:
1. A formaldehyde absorbent, comprising:
0.1-99.9 wt % of an amino acid;
99.9-0.1 wt % of a DNA or RNA base; and
0.1-10% water-soluble inorganic salt.
2. The formaldehyde absorbent according to claim 1, wherein the amino acid is selected from the group consisting of alanine, valine, leucine, isoleucine, proline, phenylalanine, tryptophan, methionine, glycine, serine, threonine, tyrosine, cysteine, asparagine, glutamine, arginine, histidine, aspartic acid, glutamic acid and a combination thereof.

3. The formaldehyde absorbent according to claim 1, wherein the DNA or RNA base is selected from the group consisting of adenine, guanine, cytosine, thymine, uracil and a combination thereof.

4. The formaldehyde absorbent according to claim 1, wherein the amino acid is a kind of amino acid metal salts, the amino acid metal salts include alkali metal salts, alkaline earth metal salts and transition metal salts.

5. The formaldehyde absorbent according to claim 4, wherein the alkali metal salts are lithium salt, sodium salt, potassium salt, rubidium salt or cesium salt, the alkaline earth metal salts are beryllium salt, magnesium salt, calcium salt, strontium or barium salt, the transition metal salts are ferric salt and zinc salt.

6. The formaldehyde absorbent according to claim 1, wherein the water-soluble inorganic salt is Silicon, oxygen, aluminum composition, or silicon, oxygen, sodium composition, or silicon, oxygen, potassium composition, or silicon, oxygen, aluminum, sodium composition, or silicon, oxygen, aluminum, potassium composition, or oxygen, silicon, potassium, sodium composition.

7. The formaldehyde absorbent according to claim 1, wherein a pH value of the formaldehyde absorbent is from 7.5 to 12.5.

8. The formaldehyde absorbent according to claim 7, wherein a pH value of the formaldehyde absorbent is from 9 to 11.

9. The formaldehyde absorbent according to claim 1, wherein the formaldehyde absorbent further comprises an additive, and the additive includes essence, pigment and antiseptic.

10. A method of absorbing formaldehyde using a formaldehyde absorbent according to claim 1, comprising:
   a. obtaining a solution by dissolving the formaldehyde absorbent in a solvent or obtaining a solid by dissolving the formaldehyde absorbent in a solvent to form a second solution and then mixing the second solution onto a solid carrier;
   b. placing the solution or the solid in an indoor space that contains formaldehyde; and
   c. contacting and reacting formaldehyde-containing air with the solution or the solid.

11. The method according to claim 10, wherein the solvent comprises water and protic solvent.

12. The method according to claim 11, wherein the protic solvent comprises at least one selected from the group consisting of glycerol, glycerol derivative and ionic liquid.

13. The method according to claim 10, wherein the solid carrier includes cloth or cotton paper.

14. The method according to claim 10, wherein the solution in step b is contained in a container and stirred constantly.

* * * * *